United States Patent [19]

Nakamura et al.

[11] Patent Number: 4,670,568

[45] Date of Patent: Jun. 2, 1987

[54] PROCESS OF PRODUCING N-FORMYLASPARTIC ANHYDRIDE

[75] Inventors: Masao Nakamura, Yokohama; Hideo Takeda, Inagi; Toshihide Yukawa, Yokohama; Haruo Kawasaki, Tokyo, all of Japan

[73] Assignee: Ajinomoto Co., Inc., Tokyo, Japan

[21] Appl. No.: 792,553

[22] Filed: Oct. 29, 1985

[30] Foreign Application Priority Data

Dec. 7, 1984 [JP] Japan ................................ 59-258765

[51] Int. Cl.$^4$ .......................................... C07D 307/66
[52] U.S. Cl. ................................. 549/253; 204/157.62
[58] Field of Search ..................... 549/253; 204/157.62

[56] References Cited

U.S. PATENT DOCUMENTS

| | | | |
|---|---|---|---|
| 3,497,005 | 2/1970 | Pelopsky et al. | 204/157.62 |
| 4,526,985 | 7/1985 | Giobbio et al. | 549/253 |
| 4,550,180 | 10/1985 | Takemoto et al. | 549/253 |

OTHER PUBLICATIONS

Morrison et al., Organic Chemistry, 4th Ed., Allyn & Bacon, Inc., pp. 54–59 (1983).

*Primary Examiner*—Henry R. Jiles
*Assistant Examiner*—Bernard I. Dentz
*Attorney, Agent, or Firm*—Oblon, Fisher, Spivak, McClelland & Maier

[57] ABSTRACT

A process for producing N-formylaspartic anhydride, which comprises, grinding solid aspartic acid into fine particles; and then reacting said finely ground aspartic acid with formic acid and acetic anhydride.

8 Claims, No Drawings

4,670,568

PROCESS OF PRODUCING N-FORMYLASPARTIC ANHYDRIDE

BACKGROUND OF THE INVENTION

1. Field of the Invention

The present invention relates to a process of producing N-formylaspartic anhydride by reacting aspartic acid with formic acid and acetic anhydride.

2. Description of the Background

A process which is known for the production of N-formylaspartic anhydride involves the reaction of aspartic acid with a large excess of formic acid and acetic anhydride, after which an aromatic hydrocarbon and/or halogenated hydrocarbon is added to the reaction mixture. Product N-formylaspartic anhydride is then isolated from the medium. (Published Unexamined Japanese Patent Application 91210/76). Another process involves the reaction of aspartic acid with formic acid and acetic anhydride in essentially stoichiometric amounts. However, a substantially longer reaction time of 48 to 60 hours is required (Published Unexamined Japanese Patent Application 46279/84).

However, the above described processes are not satisfactory from the industrial viewpoint, because the mother liquor which remains can only be treated with difficulty because of the use of formic acid in large excess amounts, or because an aromatic hydrocarbon and/or halogenated solvent is employed, or because a very prolonged reaction time is required, even though formic acid and acetic anhydride are used as reactants in stoichiometric amounts. A need therefore continues to exist for a method of preparing N-formylaspartic anhydride in improved yields and shorter reaction times.

SUMMARY OF THE INVENTION

Accordingly, one object of the present invention is to provide a method of preparing N-formylaspartic anhydride in improved yields at short reaction times.

Briefly, this object and other objects of the present invention as hereinafter will become more readily apparent can be attained in a method of preparing N-formylaspartic anhydride by grinding solid aspartic solid into fine particles, and then reacting the finely ground aspartic acid with formic acid and acetic anhydride.

DETAILED DESCRIPTION OF THE PREFERRED EMBODIMENTS

As a result of extensive investigations which have been conducted to overcome the above described problems and in order to provide an industrially satisfactory process for producing N-formylaspartic anhydride, it has now been discovered that N-formylaspartic anhydride can be produced in a short period of time in high yields if solid aspartic acid, prior to its reaction with formic acid and acetic anhydride, is ground into fine particles. This procedure obviates any necessity of using an aromatic hydrocarbon and/or halogenated hydrocarbon solvent even when acetic anhydride is only used in small amounts.

An important feature of the present invention then is that aspartic acid, which may be either a racemic mixture or in one of its optically active forms, is ground into fine particles. By initially grinding the aspartic acid, the advantages which are provided are that N-formylaspartic anhydride can be produced in shortened periods of time in high yields. Moreover, formic acid and acetic anhydride can be used in the reaction in small amounts.

The aspartic acid which is employed, can be obtained by a conventional process such as by neutralizing a solution obtained by the enzyme catalyzed reaction of fumaric acid. Upon crystallizing aspartic acid from such a solution, the acid has a particle size larger than 75 microns in amounts of 80% or more as shown in Table 1. Subsequently, the particulate aspartic acid is ground into particles of fine size in a device such as a mortar. The ground aspartic acid is then sieved into a number of particle size ranges.

TABLE 1

| Particle Size Distribution of Aspartic Acid | | | | |
|---|---|---|---|---|
| 74 microns ≧ | 74–100 | 100–150 | 150–300 | 300 ≦ |
| 19.1% | 13.2 | 16.8 | 20.4 | 20.5 |

Samples of aspartic acid of the different particle size ranges shown above were reacted under the conditions shown in Example 1 in order to examine the relationship between the particle size of the crystals and the yield of N-formylaspartic anhydride. As shown in Table 2, the results reveal that as the particle size of aspartic acid crystals is reduced, N-formylaspartic anhydride is obtained in increasingly shorter periods of time in increasingly higher yields.

The smaller the particle size of the crystals, the better the results obtained. Accordingly, the particle size of the aspartic acid should generally be smaller than 75 microns, preferably smaller than 50 microns, most preferably 10 microns. While the particle size, as stated above, should be less than 75 microns, the presence of aspartic acid particles having a size greater than 75 microns in small amounts (less than about 10%) is not objectionable or detrimental.

Aspartic acid in fine particle sizes can easily be obtained by any one of several different methods. For example, aspartic acid can be ground into fine particles by mechanical means such as by grinding crystals of aspartic acid with a griner, or by emulsifying a mixture of aspartric acid crystals, formic acid and acetic anhydride in a homogenizer, or the like.

Another alternative is to pulverize aspartic acid with a wet grinder during the course of the reaction.

Formic acid and acetic anhydride, which are used as reactants in the present process, may be incorporated in the reaction mixture in amounts of 1 to 1.5-fold mols of formic acid and 2 to 2.5-fold mols of acetic anhydride, based on aspartic acid.

When the reaction of the present invention is carried out in the presence of oxides, hydroxides or salts of various metals as catalysts, it is sufficient that the formic acid and acetic anhydride reactants are normally employed in stoichiometric amounts, i.e., 1 to 1.1-fold molar amounts of formic acid and 2 to 2.1-fold molar amounts of acetic anhydride. Suitable metal compounds which can be used as catalysts include oxides or hydroxides of various metals such as the alkali metals including lithium, sodium, potassium, and the like; the alkaline earth metals including magnesium, calcium, and the like; the copper group elements including copper, and the like; the zinc group elements including zinc, and the like; the boron group elements including aluminum, and the like; the iron group elements including iron, and the like; or salts of the metals derived from various acids such as, for example, the carbonates, carboxylates such as acetate, and the like, hydrochlorides (chlorides), hydrobromides (bromides), nitrates, phosphates, sulfates, and the like. (Published Unexamined Japanese Patent Application 175484/84).

There is no particular limitation to the amount of catalyst employed in the reaction. However, the amount of catalyst used is such that it does not adversely affect subsequent steps. The amount of catalyst may vary somewhat depending upon the kind of compound employed as a catalyst. When magnesium acetate is used as the catalyst as shown in Example 2, the amount employed is 0.005-fold mols based on L-aspartic acid. It has been observed that magnesium acetate is effective even in extremely small amounts. The optimum amount of any given compound employed as a catalyst in industrial scale operation can be easily determined by one skilled in the art by preliminary experiments prior to actually conducting full scale operations. The catalyst usually is added to the reaction system at the initiation of the dehydration reaction. Alternatively, the catalyst may be added to the system during the course of the reaction.

A preferred embodiment of the process is to conduct the reaction while subjecting the materials within the reactor to ultrasonic waves. N-formylaspartic anhydride can be obtained in higher yield by this technique. The frequency of the ultrasonic waves should be greater than 10 KHz. In fact, the greater the better. However, a sufficient effect can be achieved even when using a conventional ultrasonic wave cleaner which emits waves at a frequency of 20 to 50 KHz.

With regard to the reaction temperature, the same should range between 100° C. and 10° C., preferably between 80° C. and 20° C.; this is from the viewpoint of minimizing racemization of the product as much as possible.

As discussed above, use of the process of the present invention provides for the production of N-formylaspartic anhydride in shorter periods of time in high yields even when formic acid and acetic anhydride are used in small amounts.

Having generally described this invention, a further understanding can be obtained by reference to certain specific examples which are provided herein for purposes of illustration only and are not intended to be limiting unless otherwise specified.

EXAMPLE 1

To a solution prepared by adding 42.9 g (0.42 mols) of acetic anhydride to 13.8 g (0.30 mols) of formic acid was added 26.6 g (0.2 mols) of L-aspartic acid having a particle size of 150 to 300 microns. While stirring, the reaction was carried out while maintaining the temperature at 45° C. Sampling of the reaction was conducted with the passage of time in order to measure the rate at which N-formylaspartic anhydride is formed.

The analysis of N-formylaspartic anhydride is performed as follows: N-formylaspartic anhydride is reacted with methanol to form the α- and β-methyl ester compounds. The ester compounds are quantitatively determined by high speed liquid chromatography, from which data, the yield of N-formylaspartic anhydride can be calculated.

The highest yields and reaction times obtained were 87.5% and 24 hours for the above-described reaction.

Similar runs were carried out employing L-aspartic acid of varying particle sizes. The results are shown in Table 2 below.

TABLE 2

| Particle Size, Yield and Reaction Time of Aspartic Acid | | |
|---|---|---|
| Particle Size of L-Asp | Reaction Time | Yield |
| 150–250μ | 24 hrs. | 87.5% |
| 35–75μ | 12 | 90.6 |
| 2–10μ | 8 | 91.7 |

EXAMPLE 2

To a solution prepared by adding 64.3 g (0.63 mols) of acetic anhydride to 15.2 g (0.33 mols) of formic acid was added 39.9 g (0.3 mols) of L-aspartic acid having a particle size of 35 to 75 microns. Then 0.322 g (0.0015 mols) of magnesium acetate tetrahydrate was added to the mixture. While stirring, the reaction was carried out for 8 hours while maintaining the temperature of the reaction medium at 45° C. The yield of N-formylaspartic anhydride was 92.1%.

EXAMPLE 3

The procedure of Example 2 was repeated with the reaction being conducted for 8 hours. The reaction medium was irradiated with ultrasonic waves from an ultrasonic wave generator (manufactured by Sharp Co., Ltd., Model UTB-152, frequency of 28 KHz, output of 150 W). The yield of N-formylaspartic anhydride was 95.7%.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for producing N-formylaspartic anhydride, which comprises:
   grinding solid aspartic acid into fine particles, whereby said particles have a size of 75 μm or less; particles with formic acid and acetic anhydride, wherein the amount of formic acid ranges from 1 to 1.5 moles and the amount of acetic anhydride ranges from 2 to 2.5 moles, each per mole of aspartic acid.

2. The process of claim 1, wherein said reaction is promoted by a metal oxide, a metal hydroxide or a metal salt catalyst.

3. The process of claim 2, wherein said catalyst is an oxide, hydroxide or salt of an alkali metal, an alkaline earth metal, a copper group metal, a zinc group metal, a boron group element, or an iron group metal, said metal salt being a carbonate, carboxylate, chloride, bromide, nitrate, phosphate or sulfate.

4. The process of claim 1, wherein said particle size is less than 50 microns.

5. The process of claim 1, wherein the reaction temperature ranges from 10° C. to 100° C.

6. The process of claim 5, wherein said reaction temperature ranges from 20° C. to 80° C.

7. The process of claim 1, wherein the reaction medium is subjected to ultrasonic waves as the reaction progresses.

8. The process of claim 7, wherein the frequency of said ultrasonic waves is greater than 10 KHz.

* * * * *

UNITED STATES PATENT AND TRADEMARK OFFICE
CERTIFICATE OF CORRECTION

PATENT NO. : 4,670,568

DATED : June 2, 1987

INVENTOR(S) : MASAO NAKUMURA ET AL

It is certified that error appears in the above-identified patent and that said Letters Patent is hereby corrected as shown below:

In column 1, line 6, after "Field of the Invention" insert --:--;

In column 1, line 11, after "Description of the Background" insert --:--:

In column 1, line 44, after "aspartic" delete "solid" and insert --acid--:

In column 2, line 42, delete "griner" and insert --grinder--;

In column 3, line 17, delete "operation" and insert --operations--;

In column 4, line 43, before "particles" insert --reacting said--.

Signed and Sealed this

First Day of March, 1988

Attest:

DONALD J. QUIGG

*Attesting Officer*  *Commissioner of Patents and Trademarks*